United States Patent [19]

Marx et al.

[11] 4,173,224
[45] Nov. 6, 1979

[54] AUTOMATED INTRAVENOUS FLUID REGULATING AND ADMINISTERING APPARATUS

[75] Inventors: Alvin J. Marx, Rochester; Abraham Edelman, New York, both of N.Y.

[73] Assignee: Alvin J. Marx, Rochester, N.Y.

[21] Appl. No.: 916,836

[22] Filed: Jun. 19, 1978

Related U.S. Application Data

[63] Continuation-in-part of Ser. No. 802,891, Jun. 2, 1977, Pat. No. 4,111,198.

[51] Int. Cl.² .............................................. A61M 5/14
[52] U.S. Cl. ........................ 128/214 E; 128/DIG. 13
[58] Field of Search ................... 128/214 E, DIG. 13

[56] References Cited

U.S. PATENT DOCUMENTS

| | | | |
|---|---|---|---|
| 3,563,090 | 2/1971 | Deltour | 128/214 E |
| 3,609,379 | 9/1971 | Hildebrandt | 128/214 E |
| 4,038,981 | 8/1977 | Lefevre et al. | 128/214 E |
| 4,038,982 | 8/1977 | Burke et al. | 128/214 E |

*Primary Examiner*—William E. Kamm
*Attorney, Agent, or Firm*—Hopgood, Calimafde, Kalil, Blaustein & Lieberman

[57] ABSTRACT

Automated dispensing apparatus is disclosed for administering intravenous fluid to a patient at a controlled volumetric rate such that deviations from the desired fluid volumetric flow rate are automatically corrected. In accordance with the invention, the width and silhouette of each drop of fluid are measured and give rise to representative signals of each such parameter. These signals are then multiplied to obtain a signal proportional to the volume of the drop. This drop volume signal is combined with a rate control signal to modify the latter to reflect deviations in the measured drop volume from a nominal value. The thus modified control signal is compared against the actual rate of drop administration, and any necessary adjustment made in the constriction of a fluid-passing tube. The rate at which intravenous fluid is supplied to the patient is thus maintained at the desired volumetric rate.

11 Claims, 4 Drawing Figures

4,173,224

AUTOMATED INTRAVENOUS FLUID REGULATING AND ADMINISTERING APPARATUS

DISCLOSURE OF THE INVENTION

This application is a continuation-in-part of Ser. No. 802,891, filed on June 2, 1977 now U.S. Pat. No. 4,111,198. This invention relates to medical electronics and, more specifically, to improved intravenous flow regulation apparatus.

The intravenous administration of nutrients, electrolyte solution, and/or the like in the form of liquid drops is a common practice, particularly for postoperative patients. Such a fluid delivery system typically comprises a source container, a drop chamber, tubing, and an administrating needle.

The introduction of fluids intravenously is commonly specified by the physician in volumetric units, such as cc per hour, but, in practice, the actual flow rate of intravenous fluid may vary markedly, primarily as a result of the patient's movements during intravenous feeding. Such patient movement is likely to retard to flow of intravenous fluid to the patient, or to cease the flow of intravenous fluid altogether in the event the needle becomes obstructed. The patient's movements may also cause the intravenous fluid to flow too rapidly or at too great a rate such as when the patient changes position. In either event, the patient does not receive the proper amount of nutrient or the like and, in extreme cases, this may result in the death of the patient.

In the aforesaid co-pending application, a system is described for automatically controlling the flow of intravenous fluid by maintaining the rate, such as in drops per hour, at which drops of fluid are applied to the patient at a preset level. Thus, if the fluid is being applied at too great a rate, that condition is sensed and the tube flow resistance is automatically increased, thereby to decrease the fluid flow rate. Conversely, when the fluid flow rate is sensed as being below the desired level, the fluid tube flow resistance is automatically reduced, thereby to increase the drop rate to the desired value.

This system is effective to ensure administration of the desired drop rate of intravenous introduction of fluids. However, for this system to be totally effective to achieve the desired volumetric control over the rate of fluid introduction to the patient, the fluid drops must be normalized for drop volume.

It is an object of the present invention to provide improved intravenous fluid administering apparatus.

More specifically, it is an object of the present invention to provide improved automated intravenous injection apparatus which automatically controls the volumetric fluid administration rate.

The above and other objects of the present invention are realized in an automated intravenous fluid administration apparatus which regulates the rate of fluid flow by the selective constriction of a fluid passing tube. A drop sensor circuit monitors the rate at which the fluid is being administered and also measures the volume of each drop. The measured drop volume is used to make any necessary modification to the fluid flow rate to ensure accurate and automatic control over the volumetric rate of intravenous fluid flow to the prescribed level.

The above and other features and advantages of the present invention will become more clear from the following detailed description of a specific illustrative embodiment thereof, presented hereinbelow in conjunction with the accompanying drawings, in which.

Figure 1:
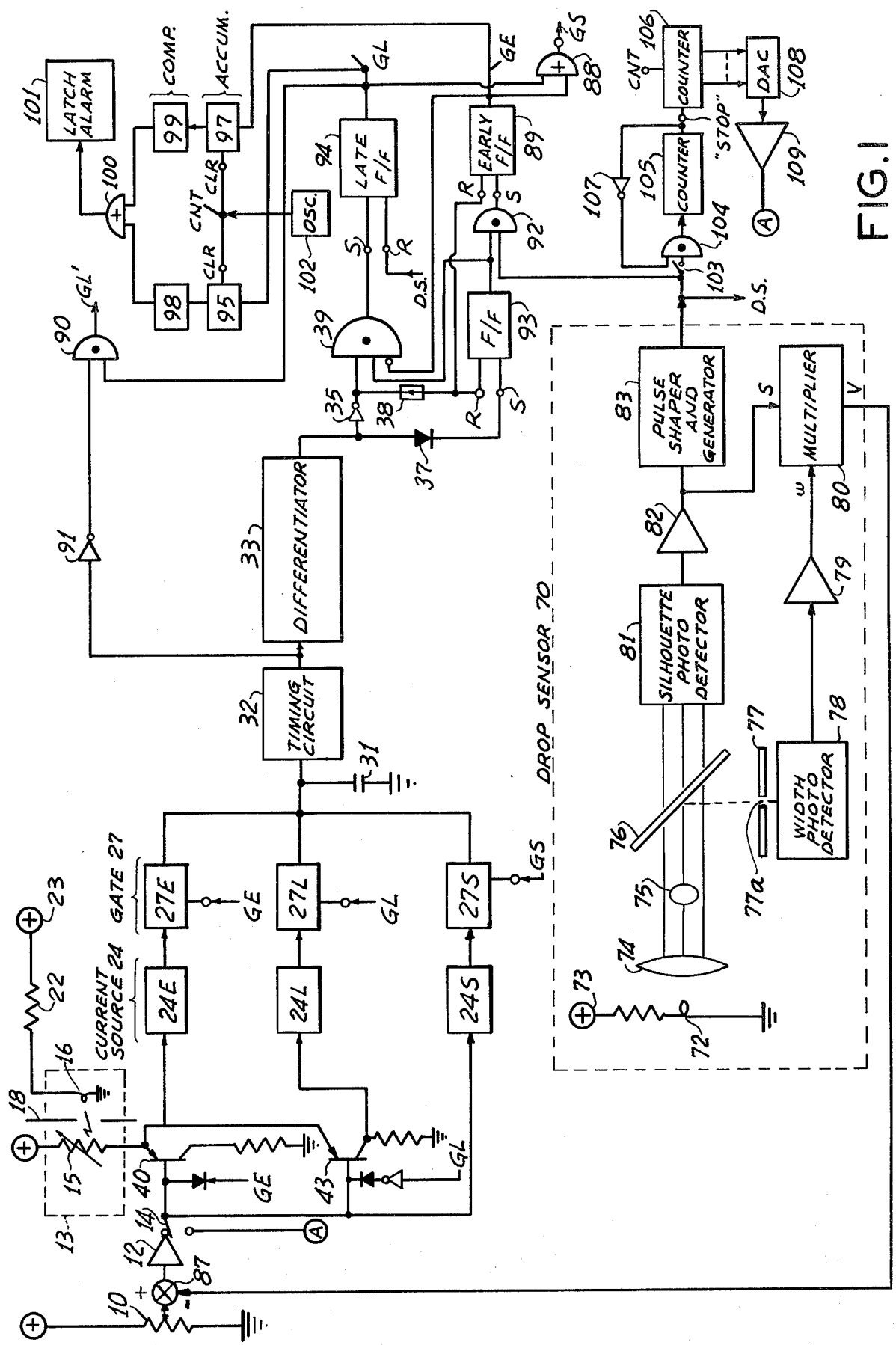
FIG. 1 is a schematic diagram of automated intravenous fluid administering apparatus in accordance with the principles of the present invention.

Referring now to FIG. 1, there is schematically shown an automated and regulated apparatus for intravenously injecting a fluid, such as an electrolyte solution, nutrients, or the like, into a patient, the volumetric or flow rate of administration (typically measured in cc per hour) being specified by the setting of an input potentiometer 10. The rate signal developed by the setting of potentiometer 10 is based on an assumed or nominal volume of each drop.

Figure 2:
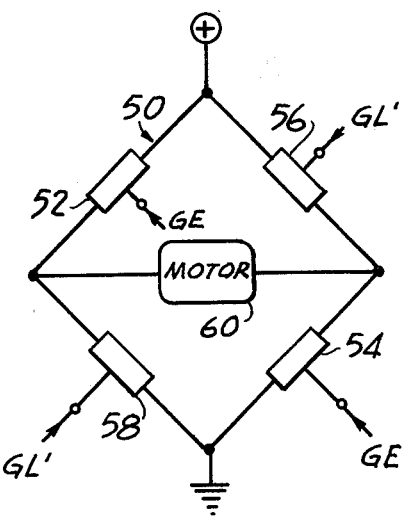
FIG. 2 is a schematic diagram of the bidirectional motor control circuit of the apparatus of the invention.

The apparatus employs a bidirectionally operative motor 60 (FIG. 2), which drives a clamping mechanism, as by a worm gear, to partially pinch off fluid-delivering tubing to a proper degree such that the actual volumetric fluid flow rate to the patient is that specified by the potentiometer 10. To the extent that the actual flow rate, as measured in terms of the rate of drops per unit time, deviates from the specified rate, as adjusted to compensate for any deviations in the volume of the fluid drops from the nominal drop volume, the apparatus, in a manner more fully discussed below, causes the motor 60 to turn in a direction, and by an amount, to cause the proper fluid flow rate by varying the inner delivery tube cross-sectional area, and thus its flow resistance. Thus, the motor 60 is made to move in a direction either to unconstrict the tubing, i.e., create a larger inner cross section to increase the rate of fluid flow, if it is determined that the volumetric flow rate is less than the rate specified by the setting of potentiometer 10, or to pinch off the tube (reduce its inner cross-sectional area) if fluid is flowing at too high a rate, that is, greater than the desired rate as established by the setting of potentiometer 10.

To this end, signals represnenting both the incidence of each fluid drop as well as the volume of each drop are developed by a drop sensor 70. For the first purpose, sensor 70 supplies a pulse that signals the incidence of each drop, and for the second purpose, it produces an analog signal that is representative of the volume of each drop. The drop volume signal is combined with the input command rate signal produced by the potentiometer 10 to modify the rate command signal in accordance with the measured drop volume. Thus, if the measured drop volume is greater than the nominal volume, the rate command signal is effectively decreased since a reduced rate of drops of a relatively higher volume will provide the desired fluid volume rate. Conversely, if the measured drop volume is less than the nominal drop volume, the effective rate signal is increased, thereby to increase the drop flow rate to, in turn, the volume flow rate to the desired level.

The modified rate signal is compared to the actual measured drop rate and, if necessary, changes are made in the fluid delivery tube to compensate for any deviations between the actual and desired fluid flow rate as represented by the drop volume-modified rate control signal. Thus, for example, if the combined rate and drop volume signals indicate that the volume per unit time of fluid being administered is too low, the tube constriction is reduced, and, conversely, if the measured flow rate is too high, the tube constriction is increased.

The drop sensor 70 includes a light source 72, which is preferably a pulsed or constant light-emitting diode or an infrared emitter, energized by a voltage source 73. The pulsed diode eliminates interference by room light. A collimating lens 74 is interposed between light source 72 and the path of a drop 75 of intravenous fluid. The lens 74 collimates the light from light source 72 to provide a beam of substantially uniform cross section and intensity, which is incident on the drop and onto a surface of a beam splitter 76. The latter, which may advantageously be a glass plate with a dichroic coating or a partially reflective coating, has the characteristic of transmitting nearly half the light incident thereon, and reflecting nearly half of the incident light.

The portion of the incident light reflected from beam splitter 76 is passed through an apertured mask 77 onto a width photodetector 78, which may be a photocell. The output of photodetector 78 is applied to the input of a buffer amplifier 79, the output of which is applied to one input of a multiplier 80, which may be of any conventional design or arrangement.

The light transmitted through beam splitter 76 is incident upon a silhouette photodetector 81, which, like photodetector 78, may be in the form of a photocell. The output of photodetector 81 is applied to the input of a buffer amplifier 82, the output of which is applied to the other input of multiplier 80. The output of amplifier 82 is also applied to the input of a pulse shaper and generator 83.

When a fluid drop 75 passes in the drop chamber between the source 72 and detector 81, it causes a momentary pulse perturbation or reduction in the light arriving at detector 81, thereby producing an electrical pulse, which is regenerated and shape-squared in a pulse shaper and generator 83, which may be of any known form, e.g., a saturated amplifier or a biased monostable trigger circuit. It will be understood that the signals produced by generator 83 and multiplier 80 respectively indicate the incidence of a drop of fluid, and the volume of each such fluid drop.

The manner in which drop sensor 70 provides a signal corresponding to the volume of the drops of intravenous fluid will now be described. Assuming that the beam of light collimated by lens has a cross section B, which is larger than the largest expected drop 75, the amount of light incident on beam splitter 76 when a drop is passing through this beam changes form B to B-S, where S represents the silhouette of the drop. If the drop has a height 2h and a width of 2w, the silhouette of the drop S is approximately equal to $\pi wh$.

This operation may be performed in silhouette photodetector 81 by establishing a preset bias or background signal level in that detector that is proportional to the value of B, such that any variation in the output of photodetector 81 is then proportional to the drop silhouette. Alternatively, an additional peak detector or sample-and-hold and summing circuit may be provided in combination with the photodetector 81 to derive the silhouette signal S from the B and B-S signals.

A signal proportional to the half-width w of the drop is obtained by passing a portion of the beam of light through the narrow slit in apertured mask 77. The width of the aperture 77a in the mask 77 is preferably the same as the beam B but the height H of the aperture is small, preferably about 10 per cent of the height of the smallest expect drop.

The width of the drop is measured by the width photodetector 78 which receives a quantity of light M when there is no drop, which is reduced to M-2wH in the presence of a drop within the beam of light. By similar means, a signal proportional to the width of the drop can be derived from the width photodetector 78.

Since the drop is approximately ellipsoidal in shape, it has a volume V equal to $4\pi w^2 h/3$. However, since $S = \pi wh$, this relationship becomes:

$$V = 4wS/3$$

Thus, the volume of the drop is proportional to the product of the silhouette S and half-width w of the drop. In the drop sensor 70 of FIG. 1, the output of the silhouette photodetector 81 is buffered in amplifier 82 and applied as the S input to multiplier 80. Similarly, the output of the width photodetector 78 is the half width signal w, which is buffered in amplifier 79 and applied at the w input of multiplier 80. By properly scaling the multiplier to reflect the necessary constant, the output of the multiplier 80 is a measure of the drop volume. The drop volume signal is applied to the minus input of summer 87, which has a plus input coupled to the movable tap of the potentiometer 10. The drop volume signal output V of multiplier 80 may be preserved between drops in any manner well known to those skilled in the art, e.g., by utilizing a peak detector, low pass filter and amplifier or the like (not shown).

As noted, if the measured volume signal is greater than that of a normal or nomimal drop of fluid, the fluid rate established by the setting of potentiometer 10 is reduced in summer 87 by a corresponding amount such that the total volumetric flow rate of intravenous fluid applied, which is a product of the rate and volume of the drops, remains substantially constant at the desired value. Conversely, if the measured drop volume signal is less than that for a nominal drop, the volume signal is correspondingly reduced such that the fluid control signal produces in summer 87 by the combination of the rate and volume signals applied to buffer amplifier 12 is increased and compared to the actual drop rate to ensure the constant desired volumetric fluid rate.

To these ends, the thus rate command signal is compared to the actual drop rate to, in turn, modify the tube constriction, if necessary, to maintain the desired drop rate, and thus the desired volumetric flow rate of fluid.

Figure 3:
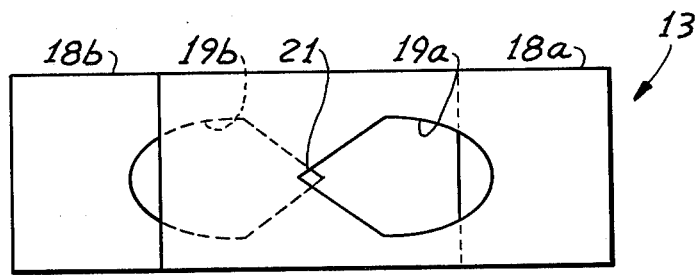
FIG. 3 is a plan view of a light sensing transducer employed in the instant invention to measure the degree of constriction of an intravenous fluid flow administering tube used in the apparatus of FIG. 1.

A tube constriction status transducer 13, such as shown in FIGS. 1 and 3, is employed to supply an electrical signal indicating the degree of construction of the fluid passing tube. The sensor 13 employs a light source 16 and a light sensitive photoresistor 15 separated by an aperture 21 between two light obstructing elements 18a and 18b. The elements 18a and 18b are respectively mechanically fixed for translation with the tube pinch-off elements, or its driver, the elements 18a and 18b respectively including apertures 19a and 19b. The light passing path from light source 16 to variable resistor 15 depends upon the common portion 21 of apertures 19a and 19b, the net effect being that the light impinging on resistor 15 and thus its electrical resistance varies with the degree of constriction of the tubing. The resistance value of resistor 15 is inversely proportional to the amount of light arriving through common aperture portion 21, and accordingly, the resistance value of resistance 15 increases with tube constriction.

Figure 4:
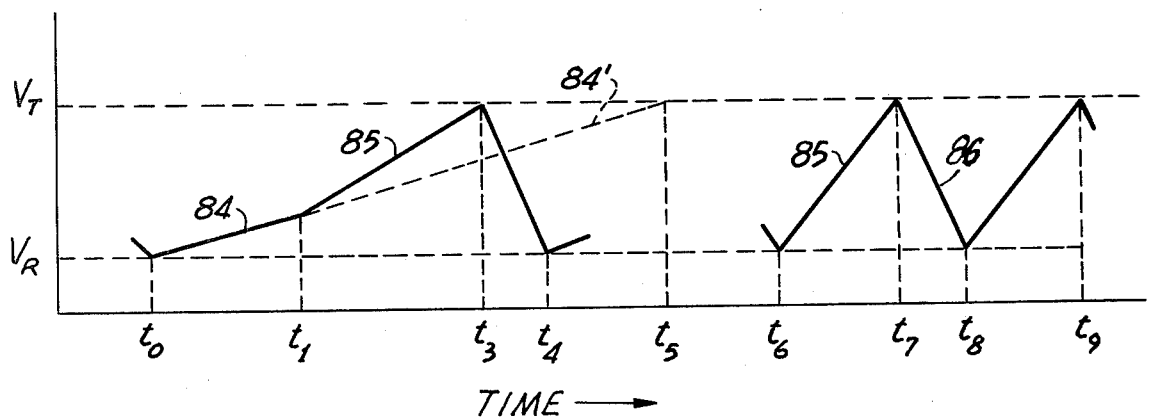
FIG. 4 is a timing diagram illustrating the operation of the apparatus of FIG. 1.

A timing diagram characterizing the operation of the system of FIG. 1 is shown in FIG. 4. At the beginning of a relaxation oscillator timing cycle, the relaxation oscillator (formed by capacitor 31 charged by one of current sources 24E, 24L, or 24S, and level triggering circuit 32 in FIG. (1) is shown beginning at a time $t_0$. The composite oscillator begins a capacitor 31 charging cycle at a rate given by curve 84-84', corresponding to a standard (S) value which assumes that fluid is being administered at a proper volume rate, i.e., that for the rate specified by the setting of potentiometer 10 as modified by the drop-volume signal. The charging capacitor 31 will not reach the triggering voltage level $V_t$ until about a time $t_5$ when the next drop arrives early (E), e.g., at a time $t_1$ rather than about the time $t_5$. When this obtains the relaxation oscilator is gated to operate at a different (typically more rapid) rate, shown by the curve segment 85, to reach the firing threshold at time $t_3$. During the time $t_1$–$t_3$, the motor 60 is energized (bridge circuit 50 in FIG. 1) in a direction to further close off the tube, thereby lessening the fluid delivery rate. The slope of the curve 85, and thereby also the active period for motor actuation, is dependent upon such factors as the prescribed fluid flow rate, the present effective cross-sectional tube area, and the degree of excess flow (amount of time the drop is early). Following the time $t_3$ the circuit resets and begins another timing operation.

The curve at the right portion of FIG. 4 characterizes circuit functioning when an insufficient fluid flow is being administered, i.e., when the drop sensor 70 supplies pulses which are "late" (L) relative to the desired fluid flow rate. During a time interval $t_6$–$t_7$, the controlling relaxation oscillator operates with a slope 85 again depending upon the parameters discussed. During the flyback interval $t_7$–$t_8$ the motor 60 is being energized in a direction to further open the tubing to correct the late drop arrival or insufficient flow rate condition. The motor activated periods 86 recur until the proper, sufficient fluid volumetric flow rate is achieved.

In the circuit shown in FIG. 1, a variable-frequency oscillator comprises the timing capacitor 31 charged by a selected one of the current sources 24E, 24L or 24S via an associated gate 27E, 27L or 27S, and a threshold timing trigger circuit 32 which fires when the capacitor 31 is charged to the threshold voltage value $V_t$. Various embodiments of the timing circuit 32 are well known to those skilled in the art, e.g., a Signetics 555 integrated circuit unit, unijunction transistor circuit, Schmitt trigger, and so forth. In particular, the gate 27E is selected by a control pulse GE to charge capacitor 31 at a rate dependent upon the current supplied by the source 24E thereof when the circuit has determined that drops are arriving early corresponding to an excessive rate of fluid administration. Similarly, current source 24L is selected by an operative control signal GL opening gate 27L when drops are late, corresponding to an insufficient fluid delivery rate; and the current source 24S is selected by gate 27S and control signal GS when the circuit is operating at the specified flow rate entered into the system by the positioning of the tap at potentiometer 10, as modified in summer 87 by drop volume signal.

When the excessive volume or early flow obtains, the active GE pulse activates controlled switches 52 and 54 (e.g. power transistors or the like) in the bridge 50 to actuate the motor 60 in a direction to drive the tube pinch-off clamp to a more closed position, as above discussed. Correspondingly, during a condition of insufficient or late flow, a modified active GL' signal activates switches 56 and 58 in the bridge 50 to energize motor 60 in an opposite direction to relieve the tube-constricting condition, thereby increasing the flow rate.

As noted, the rate signal established at the movable tap of potentiometer 10 is combined with the drop volume signal in summer 87, the output of which is buffered in amplifier 12. The output of amplifier 12 is supplied through a switch 14 as a current-controlling input signal to controlled current source 24S. The voltage-to-current converting source 24S may comprise any embodiment well known therefor for example, a voltage applied to the base of a transistor having an emitter resistor, thereby producing a current substantially equal to the ratio of the applied voltage (less the base-emitter diode drop) and emitter resistance; a voltage applied to the inverting input of an operational amplifier having a feedback resistance connecting the output and inerting input; or the like. The buffered output of summer 87 is also applied to the base of transistors 40 and 43, respectively associated with and gated on during early and late drop conditions via gating diodes, the transistors 40 and 43 similarly being controlled by the respective control signals GE and GL. For "early" or too rapid a flow rate condition processing, the fluid rate control signal output of summer 87 produces a current in transistor 40 that is substantially proportional to the base voltage applied to the transistor 40, producing a voltage at the collector of transistor 40, which is dependent upon the product of this current and the resistive state of variable resistor 15, thereby also depending upon the degree of pinch-off of the tube. The resulting potential is applied to voltage-to-current converter 24E which passes, during early condition processing, through gate 27E to the capacitor 31.

When an insufficient or late flow condition obtains, transistor 43 is activated by the GL gate pulse to supply current source 24L with a control potential which is effectively determined by the ratio of the amplifier 12 output potential divided by the resistance of variable resistance 15 (which now serves as an emitter resistance), multiplied by the collector resistance of the transistor 43.

The pulses present at the output of timing circuit 32 during flyback restoring period (times $t_3$–$t_4$, $t_7$–$t_8$, ..., of FIG. 4), assuming a low state, are differentiated by differentiator 33, and the negative pulses inverted by inverter 35. The positive differentiated output pulses are selected by positively poled diode 37. Accordingly, at the times $t_3$, $t_7$..., at the beginning of a flyback period, pulses are present at the output of inverter 35 for the assumed timer 32 - differentiator 33 operation, while pulses are present at the output of a diode 37 at the end of the flyback interval, i.e., at the times $t_4$, $t_8$... It is observed that the assumed wave polarity output of circuit 32 may be derived for any timing circuit implementation, simply employing an inverter if required.

Consider first the case where fluid is being administered at too great a volumetric rate i.e., the case considered with respect to the left portion of FIG. 4. Following the time $t_0$, the circuitry of FIG. 1 presumes that the apparatus is properly administering fluid at the specified rate and volume and thus capacitor 31 charges at the normalized rate of the curve 84, as determined by the output of current source 24S passing through the now GS signal-enabled gate 27S. The gate 27S is enabled by the GS signal developed at the output of an OR-NOT gate 88, which is activated when early condition flip-flop 89 is reset, and a GL signal supplying AND gate 90 is inactive by reason of the high output of timing circuit 32 inverted by inverter 91. At the time $t_1$, the drop sensor 70 reports that it has sensed a next drop at the time $t_1$, which is too early, i.e., which occurs before the composite relaxation oscillator has timed out (reached its threshold voltage Vt).

When this occurs, the output pulse from pulse generator 83 of drop sensor 70 activates one input of AND gate 92, the other input of which is enabled by the output of a flip-flop 93 which was previously set by the output of a diode 37 substantially at the time $t_o$. The output of AND gate 92 sets the early flip-flop 89 signaling an early drop condition. The now set early flip-flop 89 produces an active GE output pulse, shutting down the GS output of OR-NOT gate 88. The active GE signal gates on the current source 24E thus, for example, more rapidly charging capacitor 31 as shown by the curve 85 (the source 24S being blocked by the new disabled GS pulse thus deactivating gate 27S). The active GE control signal also enables gated switches 52 and 54, turning on the motor 60 in a direction to close down the tube pinching clamp as long as the GE signal persists.

At the time $t_3$, the capacitor 31 reaches its threshold value, firing circuit 32. This produces an assumed negative-going pulse at the output of differentiator 33 substantially at the time $t_3$ which passes through the inverter 35, resetting the flip-flops 93 and 89 after a small delay effected by delay circuit 38. The reset flip-flop 89 turns off the GE signal hence again creating an active standard control pulse GS to initiate another cycle after flyback. If the drop is still too early on the next cycle, the motor will again be turned on and the process will repeat until the proper tube cross-sectional value for current conditions is obtained.

Similar operation occurs for an insufficient flow condition as shown by the right portion of FIG. 4. Assuming time out of the relaxation oscillator with no encountered drop, the differentiated pulse passed by inverter 35 upon time out will fully enable the gate 39 which has its other inputs enabled by the set flip-flop 93 (set by diode 37 at the inception of the last timing cycle) and by the absence of a GE signal at the inverting input of the gate 39. Accordingly, the gate 39 sets the late condition flip-flop 94 producing an active GL signal which inhibits the development of the standard signal GS. The active GL signal causes capacitor 31 charging with the slope 85 depending upon the output of the current source 24L. The set late flip-flop also enables an AND gate 95 which is fully switched by the inverter 91 inverted outputs of timing circuit 32 during flyback periods 86, to open bridge gates 56 and 58 via pulses GL' to cause motor energization in a direction to open the pinched off tubing to increase the rate of fluid flow. The late drop flip-flop 94 will remain set until a drop is sensed by drop sensor 70.

The above described arrangement has thus been shown to automatically produce an intravenous fluid flow of a value specified by a signal entered at potentiometer 10, as modified by the drop-volume signal combined with the potentiometer rate signal at summer 87, and to implement such corrections as may from time-to-time be necessary to maintain the desired volume rate should the flow of the fluid deviate from the specified value.

It is additionally desirable in the application of intravenous feeding apparatus to provide for an audio and/or visual alarm for defined conditions e.g., non-controlled conditions characterized by excessive early (GE) or late (GL') pulses corresponding to excessive or insufficient amounts of fluid being administered to the patient. To this end, accumulators 96 and 97 are provided to respectively provide output voltage states that reflect accumulations of the GE and GL' pulses. Comparators 98 and 97 sense the accumulation state of accumulators 96 and 97, respectively. When the states of the accumulators 96 and 97 exceed predetermined bounds as sensed by a comparator 98 or 99, the comparator supplies an off-normal range output which passes through an OR gate 100 to enable a latching audio and/or visual alarm 101. A time base oscillator 102 is provided to periodically clear accumulators 96 and 97. Accordingly, the out-of-range definition for excessive GE or GL pulses is predicated on the basis of the number of such pulses exceeding a maximum permissible value therefor within the period between consecutive output pulses from the time base oscillator 102.

Particular embodiments for the accumulators 96 and 97 and comparators 98 and 99 are per se well known to those skilled in the art, and may be implemented on either an analog or digital basis. More specifically, an analog accumulator may comprise a capacitor having the charge therein increased responsive to each input pulse, and where each comparator may simply comprise a difference amplifier or the like comparing the charge state of the accumulator-capacitor with a reference voltage such as supplied at the output of the potentiometer. The capacitor may be cleared by simply using the pulse output of the time base oscillator 102 to trigger a silicon controlled rectifier or the like connected in parallel with the capacitor, the rectifier extinguishing itself once the capacitor is discharged. Alternatively, a digital accumulator may simply comprise a counter having its outputs connected to a digital comparator which provides an output indication when the contents of such a counter exceed the contents of the fixed or adjustable register.

It is also noted that it is sometimes desirable to adjust the composite arrangement of FIG. 1 to preserve whatever rate of intravenous administration was theretofore being manually implemented. To this end, the attendant may simply close a switch 103 to supply a pulse responsive to each drop from sensor 70 through an initially enabled AND gate 104 and a counter 105. An initially cleared counter 106 counts output pulses from a time base source, e.g., the oscillator 102. When the counter 105 counts a preset number of intravenous fluid drops, it stops and latches the counter 106, while blocking the AND gate 104 via an inverter 107, thereby also latching up the counter 105. Accordingly, the contents of counter 106, driven by the fixed rate source, contains a measure of the rate at which the drop sensor 70 was counting drops. The output of counter 106 is converted to a rate control voltage via a digital-to-analog converter 108, is buffered by an amplifier 108, and becomes an alternate input via switch 14 in place of the rate otherwise manually inserted into the apparatus by the potentiometer 10, as modified by the drop volume signal.

The above described arrangement is merely illustrative of the principles of the present invention and numerous modifications and adaptations thereof will be readily apparent to those skilled in the art without departing from the spirit and scope of the present invention.

What is claimed is:

1. An intravenous fluid regulator apparatus comprising means for establishing a first signal establishing a desired rate of introduction of drops of intravenous fluid to a patient, means for sensing the volume of said drops of fluid and for producing a second signal bearing a relation to the drop volume, and means coupled to said volume sensing means and to said first-signal establishing means for operatively combining said first and second signals to produce a fluid control signal.

2. The apparatus of claim 1, further comprising means for sensing the rate at which fluid drops are being introduced into the patent, means for comparing the sensed actual drop rate and said fluid control signal to modify the fluid flow rate in response to a sensed deviation between the actual drop rate and the rate as established by said fluid control signal.

3. The apparatus of claim 1, in which said drop volume sensing means comprises first means for measuring a first dimension of said drop, second means for measuring a second dimension of said drop orthogonal to said first dimension, and third means coupled to said first and second measuring means for producing a signal corresponding to the product of said first and second dimensions.

4. The apparatus of claim 3, further comprising a light source producing a beam through which drops of fluid are passed, and beam separating means for transmitting a first portion of light from said beam to said first measuring means and for transmitting a second portion of said beam to said second measuring means for producing a signal corresponding to the product of said first and second dimensions.

5. The apparatus of claim 4, further comprising a mask having a narrow slot therein interposed intermediate said beam separating means and one of said first and second measuring means.

6. The apparatus of claim 5, in which said first and second measuring means respectively comprise first and second photodetectors, and said product-forming means comprises a multiplier having first and second inputs respectively operatively connected to said first and second photodetectors, the output of said multiplier being said second signal.

7. The apparatus of claim 6, in which said first signal-establishing means comprises a variable resistance element, said combining means having one input operatively connected to said variable-resistance element and a second input operatively connected to said product-forming means.

8. In combination in intravenous fluid regulator apparatus, timing circuit means including a timing capacitor, plural current sources, plural controlled gate means each selectively connecting an associated current source with said timing capacitor, fluid drop sensing means, logic means having plural inputs connected to said fluid drop sensing means and to said timing means and plural outputs each connected to a different one of said controlled gate means for selectively enabling said gate means, wherein said plural current sources include an excess fluid rate current source and a deficient rate current source, said logic means including means for enabling said gate means associated with said excess rate current source responsive to said drop sensing means sensing an early fluid drop and means for enabling said gate means associated with said deficient fluid rate current source responsive to said drop sensing means detecting a late fluid drop rate specifying means for specifying a desired fluid administration rate, means for measuring drop volume and linear summing means connected to said drop volume measuring means and said rate specifying means, said excess and said deficient rate current sources including means for supplying a current depending upon the output of said linear summing means.

9. A combination as in claim 8 further comprising driven fluid conduit constricting means, and circuit means connected to said logic means for selectively bidirectionally energizing said driven conduit constricting means.

10. A combination as in claim 9 wherein said circuit means includes a bridge having controlled switch means connected to said plural outputs of said logic means.

11. A combination as in claim 8 further comprising transducer means for signalling fluid delivery system constriction, said excess and said deficient rate current sources including means for supplying a current depending upon the output of said transducer means.

* * * * *